United States Patent [19]

Crapo et al.

[11] Patent Number: 5,747,026
[45] Date of Patent: May 5, 1998

[54] ANTIOXIDANTS

[75] Inventors: James D. Crapo, Durham, N.C.; Bruce A. Freeman, Birmingham, Ala.

[73] Assignees: University of Alabama at Birmingham Research Foundation, Birmingham, Ala.; Duke University, Durham, N.C.

[21] Appl. No.: 190,504

[22] Filed: Feb. 2, 1994

Related U.S. Application Data

[63] Continuation-in-part of Ser. No. 136,207, Oct. 15, 1993, abandoned.

[51] Int. Cl.$^6$ .......................... A61K 38/54; A61K 9/127
[52] U.S. Cl. .................... 424/94.3; 424/94.4; 424/450; 514/78
[58] Field of Search .................... 424/450, 94.3, 424/94.4; 514/78

[56] References Cited

U.S. PATENT DOCUMENTS

| | | | |
|---|---|---|---|
| 4,758,422 | 7/1988 | Quay | 424/9 |
| 4,895,719 | 1/1990 | Radhakrishnan et al. | 424/45 |
| 4,963,367 | 10/1990 | Ecanow | 424/485 |
| 5,130,245 | 7/1992 | Marklund et al. | 435/189 |
| 5,169,630 | 12/1992 | Okaya et al. | 424/401 |
| 5,171,680 | 12/1992 | Mullenbach et al. | 435/189 |
| 5,202,317 | 4/1993 | Bruice | 514/185 |
| 5,217,966 | 6/1993 | Bruice | 514/185 |
| 5,223,538 | 6/1993 | Fridovich | 514/616 |
| 5,227,405 | 7/1993 | Fridovich | 514/612 |

FOREIGN PATENT DOCUMENTS

| | | | |
|---|---|---|---|
| 0 282 899 | 9/1988 | European Pat. Off. | C12N 9/02 |
| 0 462 836 | 12/1991 | European Pat. Off. | C12N 15/53 |
| 91/04315 | 4/1991 | WIPO . | |
| 95/10185 | 4/1995 | WIPO | A01N 43/36 |

OTHER PUBLICATIONS

Pasternack et al., "Catalysis of the Disproportionation of Superoxide by Metalloporphyrins. III", Journal of Inorganic Biochemistry 15:261–267 (1981).

Oberley et al, "Anticancer activity of metal compounds with superoxide dismutase activity", Agents and Actions 15(5/6):535–538 (1984).

Kumar et al, "Radioprotection by Antioxidant Enzymes and Enzyme Mimetics", Pharmac. Ther. 39:301–309 (1988).

Weiss et al. "Evaluation of Activity of Putative Superoxide Dismutase Mimics", The Journal of Biological Chemistry 268(31):23049–23054 (1993).

Parge et al, "Atomic structures of wild–type and thermostable mutant recombinant human Cu,Zn superoxide dismutase", Proc. Natl. Acad. Sci. USA 89:6109–6113 (1992).

Lappin, "Part III Bioinorganic Studies", Inorganic Reaction Mechanisms 7:334–343 (1981).

Boissinot et al, "Rational Design and Expression of a Heparin–Targeted Human Superoxide Dismutase", Biochemical and Biophysical Research Communication 190(1):250–256 (1993).

Oury et al, "Cold–induced Brain Edema in Mice", The Journal of Biological Chemistry 268(21):15394–15398 (1993).

Oury et al, "Extracellular superoxide dismustase, nitric oxide, and central nervous system $O_2$ toxicity", Proc. Natl. Acad. Sci. USA 89:9715–9719 (1992).

Oury et al, "Establishment of Transgenic Mice Expressing Human Extracellular Superoxide Dismutase", American Review of Respiratory Disease 143(4):A515 (1991), International Conference Supplement Abstracts—No. 236.

Oury et al, "Transgenic Mice Superexpressing Human Extracellular Superoxide Dismutase Show Increased Resistance to Cold–induced Brain Edema, But are More Susceptible to Hyperbaric Oxgyen", American Review of Respiratory Disease 145(4):A713 (1992), International Conference Supplement Abstracts—No. 211.

Oury et al, "Immunocytochemical Localization of Extracellular Superoxide Dismutase in Human Lung", American Review of Respiratory Disease 147(4):A713 (1993), International Conference Supplement Abstracts—No. 246.

Oury, Tim D., "Extracellular Superoxide Dismutase and Nitirc Oxide: Transgenic and Immunocytochemical Studies", Dissertation submitted in partial fulfillment of the requirements for the degree of Doctor of Philosophy in the Department of Pathology in the Graduate School of Duke University (Jun. 17, 1993).

Ruoslahti et al, "Arg–Gly–Asp: A Versatile Cell Recognition Signal"; Cell 44:517–518 (1986).

*Primary Examiner*—John W. Rollins
*Attorney, Agent, or Firm*—Nixon & Vanderhye P.C.

[57] ABSTRACT

The present invention relates to a method of delivering antioxidants to cells and tissues and to compositions suitable for use therein. The invention also relates to methods of disease treatment involving the use of such compositions.

16 Claims, 4 Drawing Sheets

ANTIOXIDANTS

This is a continuation-in-part of Application Ser. No. 08/136,207 filed Oct. 15, 1993, now abandoned, the entire contents of which is incorporated herein by reference.

TECHNICAL FIELD

The present invention relates to a method of delivering antioxidants to cells and tissues and to compositions suitable for use therein. The invention also relates to methods of disease treatment involving the use of such compositions.

BACKGROUND

Endothelium-dependent relaxation is impaired in vessels from atherosclerotic patients (1,2) and hypercholesterolemic animal models (3–6), suggesting the functional modification of endothelium-derived relaxing factor (EDRF) in hyperlipidemia. The dynamic role of the endothelium in the regulation of vascular tone was established when it was observed that relaxation of isolated blood vessels by vasoactive agents, such as acetylcholine (ACh) and the calcium ionophore A23187, was dependent on an intact endothelium and a diffusible factor (EDRF) that stimulated cGMP-dependent relaxation of vascular smooth muscle cells (VSMC, ref 7). Nitric oxide (.NO) and EDRF share similar chemical and pharmacological properties (8) and are derived from the oxidation of a terminal guanidino-group of L-arginine (9,10).

Numerous mechanisms have been suggested for the defect in vascular relaxation in atherosclerosis and hypercholesterolemic animal models. They include an increased diffusional barrier for .NO due to intimal cell proliferation and lipid deposition (11), L-arginine depletion (3,12,13), altered endothelial cell (EC) receptor coupling mechanisms (14), and inactivation of .NO by superoxide ($O_2^-$, refs 15 and 16). Reactive oxygen species are potent pathologic mediators in atherosclerosis as well as other vascular diseases (17,18). Both $O_2^-$ and hydroxyl radical (.OH) contribute to the oxidative modification of low-density lipoproteins (i.e. LDL. VLDL, ref 19), a critical event in the development of the atherosclerotic lesion (20). In addition, reactive oxygen species have been implicated in the alterations of EC-dependent relaxation observed in atherosclerosis (21, 22).

Peroxynitrite ($ONOO^-$), a product of .NO reaction with $O_2^-$, has recently been defined as a potent oxidant and potential mediator of vascular tissue injury (23–27). Both the independent reactions of $O_2^-$ and .NO and their reaction yielding $ONOO^-$ appear to be critical to the initiation and maintenance of the atherosclerotic state and contribute to the defect in vasorelaxation.

OBJECTS AND SUMMARY OF THE INVENTION

It is a general object of the invention to provide a method of antioxidant delivery.

It is a further object of the invention to provide lipid formulations that can be used in such a method.

Further objects and advantages will be clear from the description that follows.

pH-sensitive liposomes are nontoxic formulations that efficiently deliver macromolecules intracellularly. This is accomplished by the formation of liposomal membrane lipids which destabilize at endosomal pH, thereby enhancing liposome-endosomal membrane fusion and the consequent delivery of liposomal contents to the cytosol. This is a crucial event, because most forms of tissue free radical injury occur from intracellularly-generated reactive species, thus it is imperative to intercept these cytotoxic molecules near their sites of generation. The specific use of this vehicle to deliver antioxidants to tissues can prevent vasospasm associated with vascular surgical procedures and atherosclerosis, tissue injury from ischemia-reperfusion phenomena and the pulmonary toxicity of diverse oxidants, such as those produced during acute inflammation and the therapeutic use of hyperoxia in to treat arterial hypoxia. The efficient function of pulmonary airways, i.e. prevention of brochoconstriction in asthmatics, can also be promoted by reducing oxidant levels and preserving the airway-relaxing actions of the superoxide-inactivated molecule nitric oxide.

DETAILED DESCRIPTION OF THE INVENTION

Figures 1A, 1B:
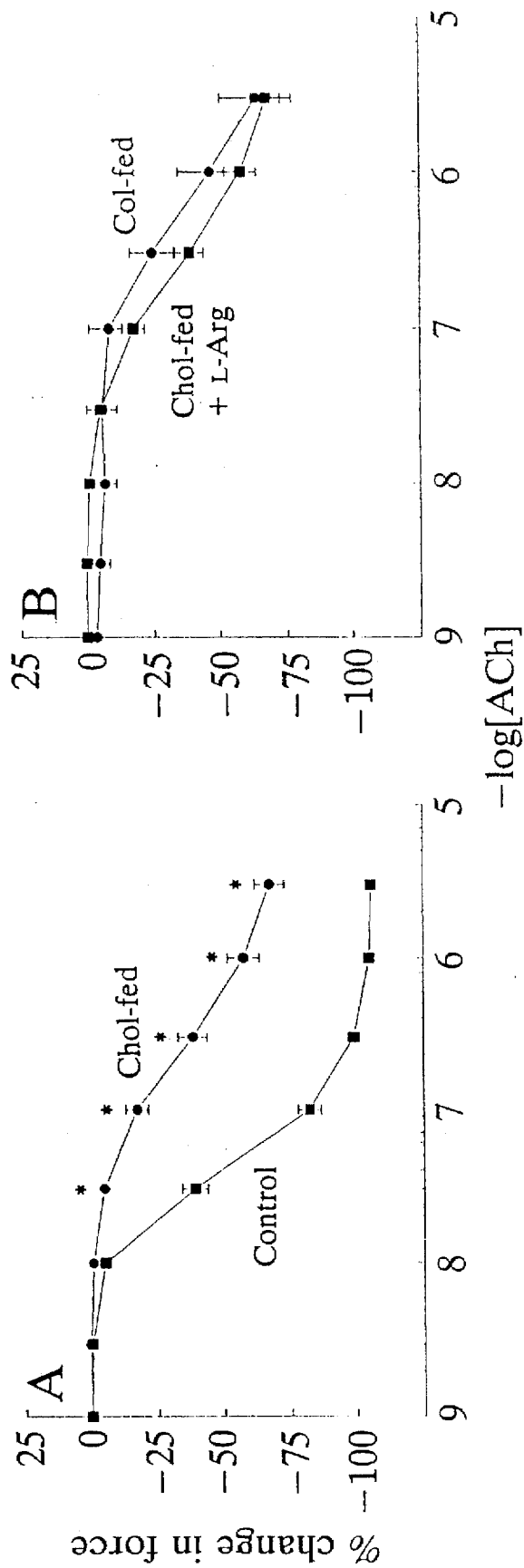
FIG. 1. Endothelium-dependent relaxation of femoral arterial ring segments from rabbits fed a 1% cholesterol diet for six months and age- and weight-matched controls. (A) Vessels from Chol-fed rabbits (●) [n=33] demonstrate an impaired maxima response to cumulative addition of ACh as well as a shift in $EC_{50}$ compared to controls (■) [n=33]. (B) Preincubation with 3 mM L-arginine (■) [n=7] for 30 min did not alter the response to ACh in vessels of Chol-fed animals. (●) [n=33]. Data are the mean±SEM. (*P<0.01).

Reactive oxygen species have been implicated in both the pathogenesis and altered physiologic responses of atherosclerosis. Oxidation of LDL, a critical event in atheroma formation, is associated with enhanced cellular production of $O_2^-$ (37, 38). Probucol's efficacy in the prevention of intimal lesion development in Watanabe hyperlipidemic rabbits is related to its antioxidant properties (39). In addition, the presence of oxidized LDL in atheromatous plaque correlates with progression of atherosclerotic cartoid disease (40). Oxidized LDL has also been shown to directly inhibit EC-dependent vasorelaxation (41, 42). Generation of $O_2^-$ in situ reduces endothelial-dependent relaxation in normal vessels (16, 43) and may be involved in the abnormal EC-dependent relaxation in atherosclerosis (22). Indirect measures of excess production of reactive oxygen species in hypercholesterolemia have been reported, including elevated levels of cholesterol oxides and oxidant-modified proteins (44, 45). However, the precise role of oxidants and their critical reaction sites in the initiation of liproprotein oxidation and impairment of vascular function in atherosclerotic processes have not been previously defined.

The data presented in the Example below indicate that a cholesterol-enriched environment enhances vascular production of $O_2^-$. This excess $O_2^-$ can then react with .NO, reducting the vasoactive levels of .NO, and diminishing the response to EC-dependent vasodilators. In this case, normal or even elevated levels of SOD may be insufficient to effectively scavenge the excess $O_2^-$. This is suggested by the slightly higher endogenous levels of SOD measured in Chol-fed animals. The hypercholesterolemic state may lead to increased expression of vessel SOD (45, 46), but in the studies described below it is not significantly different from controls. Impaired EC-dependent relaxation may then be due to enhanced reaction of .NO with $O_2^-$, yielding $ONOO^-$ (23). This reaction is rapid, with a rate constant of $k=6.7 \times 10^9 M^{-1}s^{-1}$, faster than both the SOD-catalyzed and spontaneous dismutation of $O_2^-$ to $H_2O_2$ (47). At physiological pH, $ONOO^-$ is protonated to peroxynitrous acid (ONOOH), yielding nitrogen dioxide ($.NO_2$) and a molecule with $^-OH$-like reactivity (23, 48). $ONOO^-$ has been observed to be a less potent activator of VSMC guanylate cyclase than .NO. EC-dependent relaxation thus appears to be impaired in the present model due to diminished rates of cGMP formation. Alternatively, the impaired relaxation may be the result of $ONOO^-$—derived $^-OH$, which stimulates guanylate cyclase activity to a lesser extent than .NO (49).

Peroxynitrite exhibited potent oxidative effects of β-VLDL, the principal carrier of cholesterol in this model. When compared to 5 μM $Cu^{2+}$, a commonly employed in vitro lipoprotein oxidant (50), $ONOO^-$ rapidly generated greater quantities of lipid peroxidation products. Similar results have been observed using the syndominine, SIN-1, a compound yielding .NO and $O_2^-$, which react to form $ONOO^-$(51). Thus, the product of .NO and $O_2^-$ reaction appear to play a critical role in the initiation and extension of atherosclerotic lesions as well as the altered vascular reactivity associated with the disease.

The studies described in the Example also demonstrate that pH-sensitive liposomes are effective vectors for the delivery of antioxidant enzymes to the wall of both normal and atherosclerotic vessels. Pharmacologic efficiency of Lip-SOD, as indicated by enzymatic analysis and changes in vascular function, contrasts with the minimal effect of native SOD. It is not unexpected that native SOD did little to restore EC-dependent relaxation. The 32K Da SOD is electrostatically repelled from cell surfaces at pH 7.4, and is thus excluded from intracellular compartments, where significant extents of both the production and reactions of $O_2^-$ and .NO will occur.

In the studies described below pH-sensitive liposomes facilitated delivery of SOD to internal sites of $O_2^-$ production, thus lowering steady state $O_2^-$ concentration, and limiting $O_2^-$ reaction with .NO to yield $ONOO^-$. Once injected intravenously, liposomes gain direct contact with the blood vessel wall and become incorporated via endocytosis. In the acidic environment of the endocome (pH 5.0), the liposomal membrane undergoes a phase transition (52), promoting liposome-endosome fusion and release of liposomal contents to the cytosol. An increase in SOD content was demonstrated in both control and Chol-fed liposome-injected rabbits. Parallel immunocytochemical quantitation of SOD distribution reveals that SOD gained access not only to EC, but VSMC and the interstitium as well. These locales are all critical sites of excess production of oxidants associated with the development and maintenance of atherosclerosis. Thus, Lip-SOD delivery is particularly effective in raising tissue levels of the enzyme. Use of polyethylene glycol-derivatized SOD to enhance vascular endothelial antioxidant enzyme levels has been previously employed (53). However, higher doses of PEG-SOD (41,000 U/kg/d vs. 1,500 U/k/d) were used to achieve similar results in an animal model of atherosclerosis (54).

Certain aspects of the invention are described in greater detail in the non-limiting Example that follows.

EXAMPLE

Materials

Bovine CuZn SOD was from Diagnostic Data Inc. (Mountain View, Calif.). Dioleoyl-phosphatidylethanolamine and dioleoyl-glycero-3-succinate were obtained from Avanti Polar Lipids (Birmingham, Al.). L-arginine, ACh, indomethacin, papaverine, phenylephrine and tetraethylammoniumhydroxide were from Signa Chemical Co. (St. Louis, Mo.).

Vessel Contraction Studies

New Zealand white rabbits (2.5–3.0 kg) were maintained on rabbit chow containing 1% cholesterol (Ralston Purina, Inc.) for 6 months prior to study (Chol-fed group). Age- and weight-matched controls were fed a standard diet. After exsanguination under ketamine/rompun anesthesia, vessels were isolated and changes in tension were measured in fermoral artery ring segments, as previously described (28). Following maximal contraction with 70 mM KCl and recovery, phenylephrine was added to achieve 30% of maximal tone. Rings were then exposed to increasing doses of ACh; relaxation is reported as the percent decrease in pre-existing tone. After the generation of cumulative ACh dose-response curves, rings were exposed to $3 \times 10^{-5}M$ papaverine. In some experiments, rings from control and Chol-fed rabbits were incubated with 3 mM L-arginine for 30 minutes prior to the administration of ACh. In other studies, vessels were treated with native bovine SOD (200 U/ml) before measuring ACh-induced relaxation. All studies were performed in the presence of 5 μM indomethacin.

Liposome-entrapped SOD

Liposomes were composed of dioleoyl-phosphatidylethanolamine and dioleoyl-glycero-3-succinate (1:1). Lipids were dried under $N_2$ nd hydrated 36 hr in 210 mM sucrose, 7 mM HEPES. During hydration pH 8.5 was maintained with tetraethylammoniumhydroxide. Lipids were added to SOD, dissolved in sucrose-HEPES buffer, and the mixture was extruded through a 600 nm filter under $N_2$ pressure (Extruder, Lipex Biomembranes); mean liposome diameter was 217 nm. Final SOD concentration was 3,000 U/ml. Liposomal-entrapped SOD (Lip-SOD) was injected daily (1,500 U/kg) via the marginal ear vein for 5 days before sacrifice.

Analytical Procedures

Plasma cholesterol levels were determined using an enzymatic method (29) modified for 96 well plates. Aortic SOD activity was assayed in a 10% homogenate in 50 mM KPi, 0.1 mM EDTA, 0.1% CHAPS, pH 7.8. After centrifugation at 10,000×g×10 min at 4° C., supernatant SOD activity was measured by inhibition of xanthine oxidase-mediated reduction of cytochrome c (30). Tissue DNA was measured by fluorescence (31). Femoral ring segments were prepared for quantitative electron microscopic immunocytochemistry as previously (32). Cryo-ultrathin sections were incubated with rabbit antibovine CuZn SOD (1:100 dilution) and 10 nm gold colloid conjugated to protein A. Distribution of SOD labeling was measured by counting gold granules and tissue points of randomly selected photographic fields. Because of variable loss of endothelium during cryosectioning, EC SOD density was quantitated in selected segments with intact endothelium.

β-VLDL Oxidation

Peroxynitrite was synthesized as previously (23). β-VLDL, isolated as described (33), was exposed to ONOO⁻ or 5 μM CuSO4. Lipid oxidation was assessed by measurement of thiobarbiturnc acid-reactive substances (TBARS) and formation of conjugated dienes (25).

RESULTS

Plasma cholesterol was markedly elevated in rabbits fed a 1% cholesterol diet for six months, from 43±6 to 2696±292 mg/dl. Intimal thickening was apparent, with extensive plaque deposition, about 50% of the luminal surface of the femoral artery.

Figure 2A:
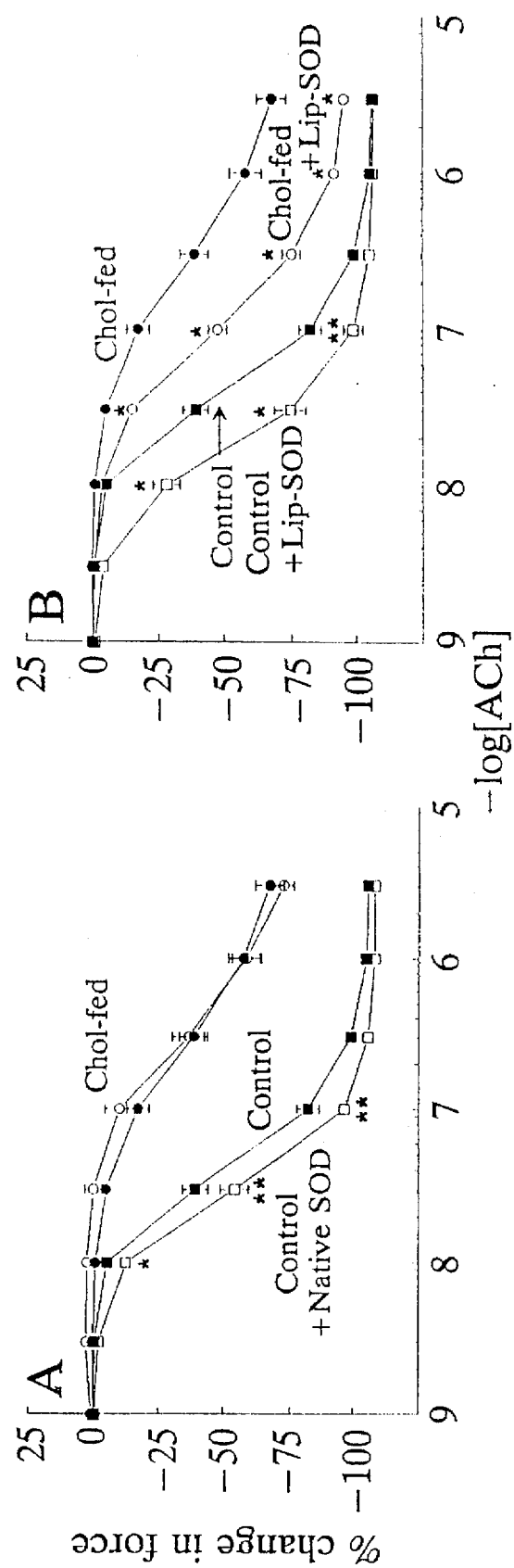
FIG. 2. Cumulative dose-response curves for ACh in femoral artery rings from Chol-fed rabbits (●) [n=33] and controls (■) [n=33]. (A) Separate groups of vessels from control (□) [n=21] and (O) [n=15] rabbits were incubated with CuZn bovine SOD (200 U/ml) before addition of ACh. Native SOD failed to improve EC-dependent relaxation in segments from Chol-fed animals. (B) Control (□) [n=20] and Chol-fed rabbits (O) [n=30] were treated with Lip-SOD for 5 days prior to study. Liposomal-SOD enhanced ACh-induced relaxation in both groups. The $\Delta EC_{50}$ for ACh-induced relaxation as well as the change in maximal relaxation was greater in the Chol-fed group. Data are presented as the mean±SEM(*P<001; **P<0.05).
Figure 2B:
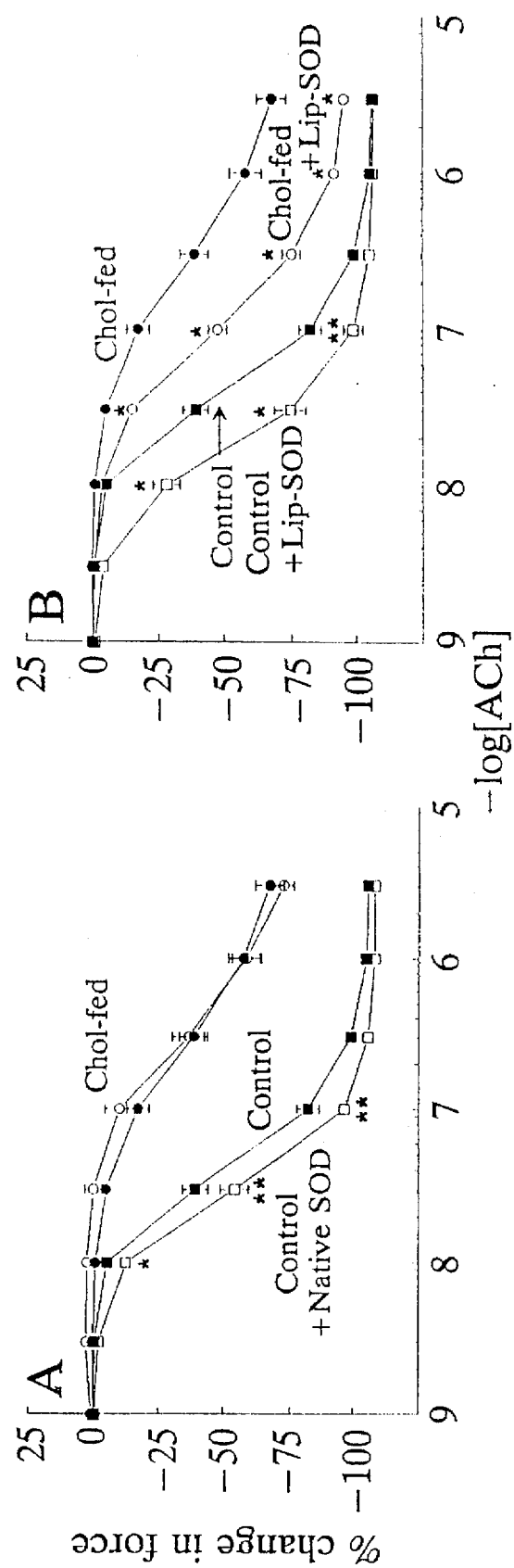

Control and Chol-fed groups exhibited no differences in the maximal tone generated with 70 mM KCl nor in the phenylephrine concentrations required to achieve submaximal contraction of vessels. Chol-fed rabbits manifested a significant shift in the $EC_{50}$ to ACh-induced relaxation: $1.73 \times 10^{-6}$M vs. $5.21 \times 10^{-8}$M (P<0.01) as well as a 33% reduction in maximal response (FIG. 1A). Incubation of ring segments with L-arginine failed to augment ACh-induced relaxation in Chol-fed rabbits (FIG. 1B). Pretreatment with native CuZn SOD had a minor effect on the ACh dose-response profile in control, but not Chol-fed rabbits (FIG. 2A). Due to the limited cellular uptake of native SOD, we delivered SOD in vivo via pH-sensitive liposomes. Vessels isolated from both control and Chol-fed rabbits treated for 5 days with Lip-SOD demonstrated enhanced ACh-induced relaxation (FIG. 2B). Liposomal-SOD restored ACh-induced relaxation in Chol-fed rabbits close to control values ($EC_{50}$; $1.65 \times 10^{-7}$M). In addition, the $\Delta EC_{50}$ for ACh-induced relaxation was greater (P<0.01) in the Chol-fed group than in the control group. Further, Lip-SOD treatment enhanced the maximum relaxation of segments to ACh in Chol-fed rabbits. Treatment of both control and Chol-fed rabbits with empty pH-sensitive liposomes had no effect on ACh responses.

There was no difference between groups in the response to papaverine, an endothelial-independent vasodilator; vessels relaxed below the initial vessel tone measured prior to phenylephrine administration: 114.52%±3.13 (control) vs. 116.35%±6.51 (Chol-fed). Lip-SOD had no effect on responses to papaverine in either group.

Figure 3A:
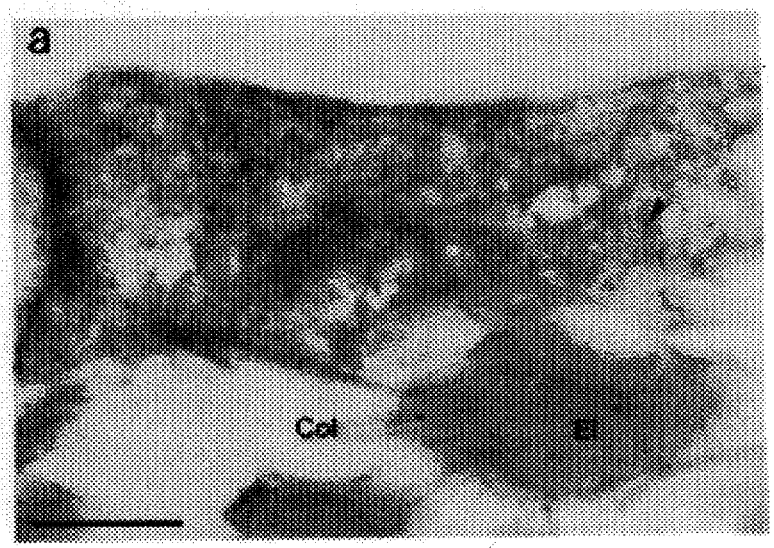
FIGS. 3A & 3B. Electron micrographs of aortic segments from control and Lip-SOD treated rabbits. (A) A small degree of cross reaction of the anti-bovine CuZn SOD to rabbit CuZn SOD was observed in the EC's from control rabbits. (B) Labeling of cryo-ultrathin sections with anti-bovine SOD (A) demonstrates enhanced SOD distribution in the endothelium, smooth muscle and extracellular matrix of the Lip-SOD treated animal. m=mitochondria; d=desmosome, Col=collagen fibrils; El=elastin. Bar=0.5 μm.
Figure 3B:
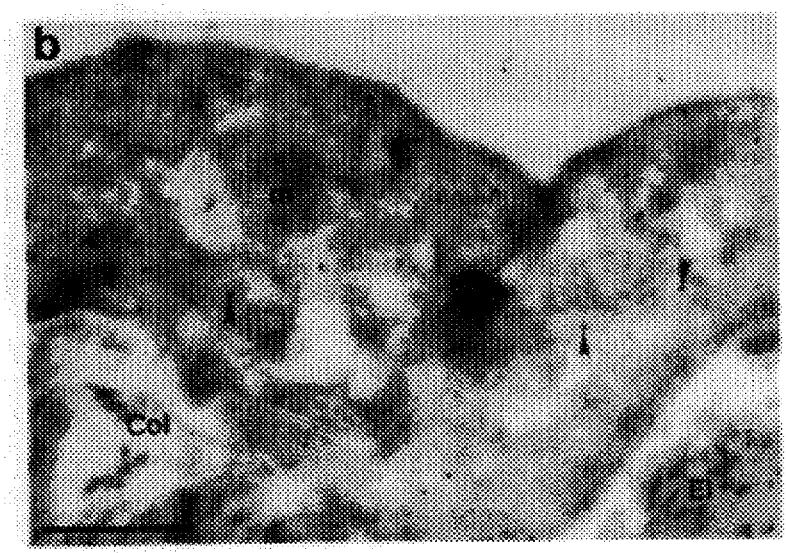

Quantitative electron microscopic immunocytocheimistry assessed the distribution of SOD in the blood vessel wall. Lip-SOD localized not only in the endothelium, but also in the subendothelial space and in underlying VSMC (Table 1, FIG. 3). A small degree of crossreactivity was evident between rabbit anti-bovine SOD and endogenous rabbit SOD. However, multivariate analysis of labeling densities showed significant increases in labeling in sections from Lip-SOD injected rabbit vessels compared with controls (Table 1). SOD activity was similar in vessel homogenates from control and Chol-fed rabbits (Table 1). Liposomal-SOD led to an almost 2-fold increase in vessel SOD activity in both groups.

Figure 4B:
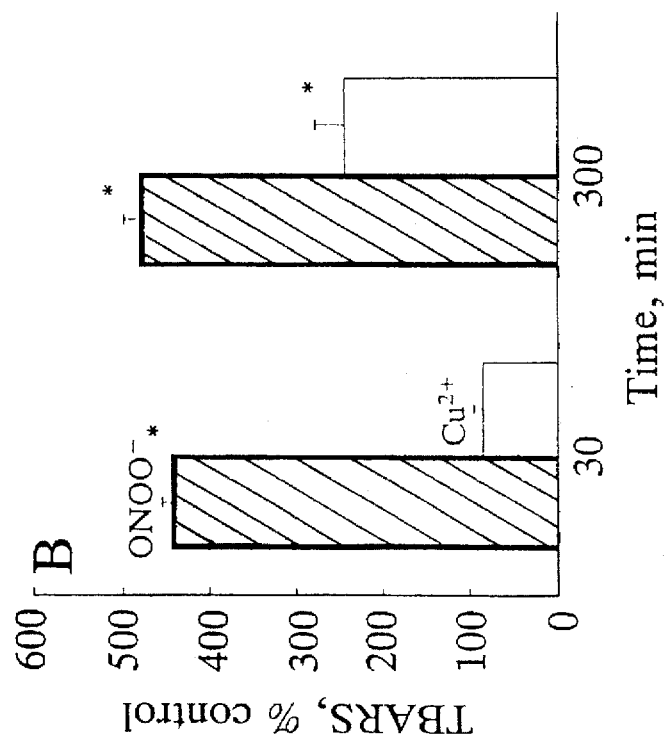
FIG. 4. Peroxynitrite-induced lipid oxidation in β-VLDL. (A) Conjugated diene formation: β-VLDL (10 μg pro/ml in 50 mnM KPi, pH 7.4) was incubated with 5 μM $Cu^{2+}$ (—) or 100 μM $ONOO^-$ (—) and the $\Delta OD_{234}$ was recorded. Tracings are representative of lipoproteins from 3 rabbits. (B) TBARS formation: β-VLDL (100 μg pro/ml in 50 mM KPi, pH 7.4, 37°) was incubated with $ONOO^-$ (■) or $Cu^{2+}$ (□). 30 min exposure to $ONOO^-$ resulted in a 4-fold increase in TBARS formation, while 5 μM $Cu^{2+}$ did not increase TBARS until 300 minutes. Data are presented as average % control±SD (n=8; *P<0.01).
Figure 4A:
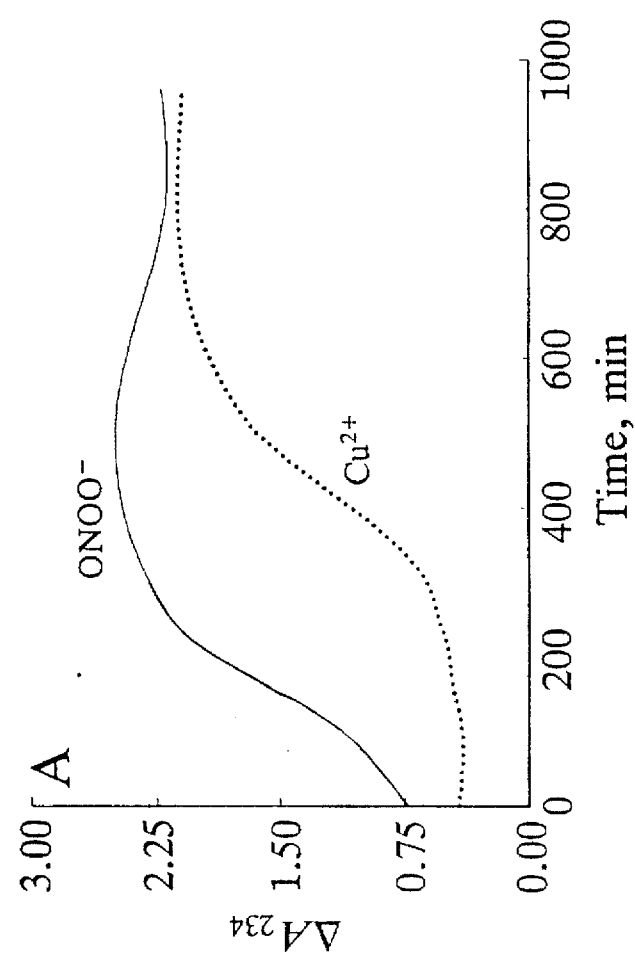

Exposure of β-VLDL to ONOO⁻ resulted in rapid generation of lipid oxidation products as indicated by both TBARS and conjugated diene formation (FIGS. 4A and 4B). Control experiments demonstrated that up to 100 μM .NO alone did not stimulate lipid peroxidation.

TABLE 1

Vascular enzymatic activity and tissue distribution of CuZn SOD delivered via pH-sensitive liposomes.

| Measurement | −SOD liposomes | | +SOD liposomes | |
|---|---|---|---|---|
| | Control | Chol-fed | Control | Chol-fed |
| ENZYMATIC ACTIVITY U SOD/μg DNA | 0.92 ± 0.13 | 1.06 ± 0.43 | 1.73 ± 0.46* | 1.73 ± 0.55* |
| TISSUE DISTRIBUTION Point density of colloidal gold particles (*10⁻²) (Relative ratio of # immunogold particles/tissue point) | | | | |
| Endothelium | | 0.70 ± 0.02 | | 1.53 ± 0.27** |
| Smooth muscle | | 0.99 ± 0.08 | | 1.88 ± 0.11** |
| Extracellular matrix | | 0.40 ± 0.12 | | 1.18 ± 0.14** |
| Collagen | | 0.31 ± 0.06 | | 1.16 ± 0.32** |
| Elastin | | 1.95 ± 0.16 | | 2.43 ± 0.33 |

SOD activity: mean ± SD of aortae from 3 animals from each group. Morphometric data: mean ± SD from analysis of 4 sites from each treatment group. Because there was no difference in SOD distribution between control and Chol-fed groups, the groups were combined and analyzed for treatment with and without Lip-SOD. (*P < 0.01; **P < 0.05)

All documents cited above are hereby incorporated in their entirety by reference.

One skilled in the art will appreciate from a reading of this disclosure that various changes in form and detail can be made without departing from the true scope of the invention.

REFERENCES

1. Bossaler, C., Habib, G. B., Yamamoto, H., Williams, C., Wells, S. & Henry, P. D. (1987) *J. Clin. Invest.* 79, 170–174.
2. Forstermann U., Mügge, A., Alheid, U., Haverich, A. & Frolich, J. C. (1988) *Circ. Res.* 62, 185–190.
3. Shimokawa, H., Kim, P. & Vanhoutte, P. M. (1988) *Circ. Res.* 63, 604–612.
4. Harrison, D. G., Freiman, P. C., Armstrong, M. L., Marcus, M. L. & Heistad, D. D. (1987) *Circ. Res.* 61(Suppl II), II-74–II-80.
5. Jayakody, L., Senaratne, M., Thomson, A. & Kappagoda, T. (1987) *Circ. Res.* 60, 251–264.
6. Chappell, S. P., Lewis, M. J. & Henderson, A. H. (1987) *Cardiovasc. Res.* 21, 34–38.
7. Furchgott, R. F. & Zawadsky, J. V. (1980) *Nature* 288, 373–376.
8. Moncada, S., Palmer, R. M. J. & Higgs, E. A. (1991) *Pharmacol. Rev.* 43, 109–142.
9. Palmer, R. M. J., Ferrige, A. G. & Moncada S. (1987) *Nature* 327, 524–526.
10. Ignarro, L. J., Buga, G. M., Wood, K. S., Byrns, R. E. & Chaudhuri, G. (1987) *Proc. Natl. Acad. Sci. USA.* 84, 9265–9269.
11. Lopez, J. A. G., Armstrong, M. L., Harrison, D. G., Piegors, D. J. & Heistad, D. D. (1989) *Circ. Res.* 65, 1078–1086.
12. Cooke, J. P., Andon, N. A., Girerd, X. J., Hirsch, A. T. & Creager, M. A. (1991) *Circulation* 83, 1057–1062.
13. Schini, V. B. & Vanhoutte, P. M. (1991) *Circ. Res.* 68, 209–216.
14. Cohen, R. A., Zitnay, K. M, Haudenschild, C. C. & Cunningham, L. D. (1988) *Circ. Res.* 63, 903–910.
15. Gryglewski, R. J., Palmer, R. M. J. & Moncada, S. (1986) *Nature* 320, 454–456.
16. Rubanyi, G. M. & Vanhoutte, P. M. (1986) *Am. J. Physiol.* 250, H815–H821.
17. Rubanyi, G. M. (1988) *Free Rad. Biol. and Med.* 4, 107–120.
18. Lindsay, S. L. & Freeman, B. A. (1990) in *Pulmonary Circulation: Normal and Abnormal,* ed. Fishman, A. P. (Univ. Penn. Press) pp. 217–229.
19. Panasenko, O. M., Vol'nova, T. V., Azizova, O. A. & Vladimirov, Y. A. (1991) *Free Rad. Biol. and Med.* 10, 37–148.
20. Schwartz, C. J., Valente, A. J., Sprague, E. A., Kelley, J. L. & Nerem R. M. (1991) *Clin. Cardiol.* 14, I-I-I-16.
21. Tagawa, H., Tomoike, H. & Nakamura M. (1991) *Circ. Res.* 68, 330–337.
22. Mügge, A., Elwell, J. H., Peterson, T. E., & Harrison, D. G. (1991) *Am. J. Physiol.* 260, C219–C225.
23. Beckman, J. S., Beckman, T. W., Chen, J., Marshall, P. A. & Freeman, B. A. (1990) *Proc. Nal. Acad. Sci. USA.* 87, 1620–1624.
24. Radi, R., Beckman, J. S., Bush, K. M. & Freeman, B. A. (1991) *J. Biol. Chem.* 266, 4244–4250.
25. Radi, R., Beckman, J. S., Bush, K. M. & Freeman, B. A. (1991) *Arch. Biochem. Biophys.* 288, 481–487.
26. Ischiropoulos, H., Zhu, L. & Beckman, J. S. (1992) *Arch. Biochem. Biophys.* 298, 446–451.
27. Radi, R., Cosgrove, T. P., Beckman, J. S. & Freeman, B. A. (1993) *Biochem. J.* 290, 51–57.
28. Ku, D. D. (1986) *J. Cardiovasc. Pharmacol.* 8, 29–36.
29. Warnick, G. R. (1986) *Meth. Enzym.* 129: 101–123.
30. McCord J. M. & Fridovich. I. (1969) *J. Biol. Chem.* 244, 6049–6055.
31. Labarca, C. & Paiger, K. (1980) *Anal. Biochem.* 102, 344–352.
32. Crapo, J. D., Oury, T., Rabouville, C., Slot, J. W. & Chang, L.-Y. (1992) *Proc. Nat. Acad. Sci. USA* 89, 10405–10409.
33. Gianturco, S. H., Bradley, W. A., Gotto, A. M., Morrisett, J. D., Peavy, D. L. (1982) *J. Clin. Invest.* 70, 168–178.
34. Harrison, D. G., Armstrong, M. L., Freiman, P. C. & Heistad, D. D. (1987) *J. Clin. Invest.* 80, 1808–1811.
35. Mügge, A. & Harrison, D. G. (1991) *Blood Vessels.* 28, 354–357.
36. Minor, R. L., Myers, P. R, Guerra, R., Bates, J. N. & Harrison, D. G. (1990) *J. Clin. Invest.* 86, 2109–2116.
37. Witztum, J. L. & Steinberg, D. (1991) *J. Clin. Invest.* 88, 1785–1792.
38. Steinbrecher, U. P. (1988) *Biochim. Biophys. Acta.* 959, 20–30.
39. Carew, T. E., Schwenke, D. C. & Steinberg, D. (1987) *Proc. Natl. Acad. Sci. USA.* 84, 7725–7729.
40. Salonen J. T., Yla-Herttuala, S., Yamamoto R., Butler, S., Korpela, H., Salonen, R., Nyyssonen, L. Palinski, W. & Witztum, J. L. (1992) *Lancet* 339, 883–887.
41. Plane, F., Kerr, P., Bruckdorfer, K. R. & Jacobs, M. (1991) *Biochem. Soc Transact.* 18, 1177–1178.
42. Jacobs, M., Plane, F. & Bruckdorfer, K. R. (1990) *Br. J. Pharmacol.* 100, 21–26.
43. Abrahamsson, T., Brandt, U., Marklund, S. L. & Sjöqvist, P. -O. (1992) *Circ. Res.* 70, 264–271.
44. Haberland, M. E., Fong, D. & Cheng, L. (1989) *Science* 241, 215–218.
45. Sharma, R. C., Crawford, D. W., Kramsch, D., Sevanian, A. & Jiao, Q. (1992) *Arteriosclerosis and Thrombosis* 12, 403–415.
46. Del Boccio, G. Lapenna, D., Porreca, E., Pennelli, A., Savini, F., Feliciani, P., Ricci, G. & Cuccurullo, F. (1990) *Atherosclerosis* 81, 127–135.
47. Huie, R. E., & Padmaja, S. (1993) *Free Rad. Res. Commun.* in press.
48. Hogg, N., Darley-Usmar, V. M., Wilson, M. T. & Moncada, S. (1992) *Biochem. J.* 281, 419–424.
49. Mittal, C. K. & Murad, F. (1977) *Proc. Natl. Acad. Sci. USA.* 74, 4360–4364.
50. Gebicki, J. M., Jurgens, G. & Esterbauer, H. (1991) in *Oxidative Stress,* ed Sies, H. (Academic Press, London, San Diego, New York), pp. 371–397.
51. Darley-Usmar, V. M., Hogg, N., O'Leary, V. J., Wilson, M. T. & Moncada, S. (1992) *Free Rad. Res. Comm.* 17, 9–20.
52. Huang, L., Connor, J. & Wang, C.-Y. (1987) *Meth. Enzym.* 149, 88–99.
53. Beckman, J. S., Minor, R. L., White, C. W., Repine, J. R., Rosen, G. M. & Freeman, B. A. (1988) *J. Biol. Chem.* 263, 6884–6892.
54. Mügge, A., Elwell, J. E., Peterson, T. E., Hofmeyer, T. G., Heistad, D. D. & Harrison, D. G. (1991) *Circ. Res.* 69, 1293–1300.

Abbreviations:

ACh, acetyichofine; SOD, superoxide dismutase; $\beta$-VLDL, $\beta$-very low density lipoprotein; Lip-SOD, liposomal-entrapped SOD; EDRF, endothelium-derived relaxing factor; VSMC, vascular smooth muscle cell; EC, endothelial cell; LDL, low density lipoprotein; Chol-fed, rabbits fed a 1% cholesterol diet; TBARS, thiobarbituric acid reactive substances.

What is claimed is:

1. A method of reducing the $O_2^-$ concentration of a cell comprising contacting said cell with a liposome having an antioxidant entrapped therewithin under conditions such that said liposome fuses with the membrane of said cell so that said antioxidant enters said cell and reacts with said $O_2^-$ thereby reducing the $O_2^-$ concentration of said cell.

2. The method according to claim 1 wherein said antioxidant is an enzyme.

3. The method according to claim 2 wherein said enzyme is superoxide dismutase.

4. The method according to claim 1 wherein said cell is an endothelial cell.

5. The method according to claim 1 wherein said cell is an interstitial cell.

6. The method according to claim 1 wherein said cell is a smooth muscle cell.

7. The method according to claim 1 wherein said liposome comprises dioleoyl-phosphatidylethanolamine and dioleoyl-glycero-3-succinate.

8. The method according to claim 7 wherein said dioleoyl-phosphatidylethanolamine and dioleoyl-glycero-3-succinate are present in a ratio of about 1:1.

9. A method of inhibiting the production of $ONOO^-$ in a cell containing $O_2^-$ and NO comprising contacting said cell with a liposome having an antioxidant entrapped therewithin under conditions such that said liposome fuses with the membrane of said cell so that said antioxidant enters said cell and reacts with said $O_2^-$ thereby preventing said $O_2^-$ from reacting with said NO to form $ONOO^-$.

10. The method according to claim 9 wherein said antioxidant is an enzyme.

11. The method according to claim 10 wherein said enzyme is superoxide dismutase.

12. The method according to claim 9 wherein said cell is an endothelial cell.

13. The method according to claim 6 wherein said cell is an interstitial cell.

14. The method according to claim 9 wherein said cell is a smooth muscle cell.

15. The method according to claim 9 wherein said liposome comprises dioleoyl-phosphatidylethanolamine and dioleoyl-glycero-3-succinate.

16. The method according to claim 15 wherein said dioleoyl-phosphatidylethanolamine and dioleoyl-glycero-3-succinate are present in a ratio of about 1:1.

* * * * *